US008664381B2

(12) United States Patent
Angeli et al.

(10) Patent No.: US 8,664,381 B2
(45) Date of Patent: Mar. 4, 2014

(54) PROCESS FOR THE PREPARATION AND PURIFICATION OF AMOROLFINE HYDROCHLORIDE

(75) Inventors: Roberto Angeli, Scandicci (IT); Marco Possenti, Firenze (IT); Salvatore Demartis, Sassari (IT)

(73) Assignee: SYNTECO S.p.A., San Martino Siccomario (IT)

( * ) Notice: Subject to any disclaimer, the term of this patent is extended or adjusted under 35 U.S.C. 154(b) by 0 days.

(21) Appl. No.: 13/202,502

(22) PCT Filed: Feb. 18, 2010

(86) PCT No.: PCT/EP2010/052047
§ 371 (c)(1),
(2), (4) Date: Aug. 19, 2011

(87) PCT Pub. No.: WO2010/094739
PCT Pub. Date: Aug. 26, 2010

(65) Prior Publication Data

US 2011/0301346 A1 Dec. 8, 2011

(30) Foreign Application Priority Data

Feb. 20, 2009 (IT) ................................ FI2009A0032

(51) Int. Cl.
*C07D 265/30* (2006.01)

(52) U.S. Cl.
USPC .......................................................... 544/178

(58) Field of Classification Search
CPC ..................................................... B01D 15/325
USPC .......................................................... 544/178
See application file for complete search history.

(56) References Cited

FOREIGN PATENT DOCUMENTS

| | | | |
|---|---|---|---|
| EP | 1 935 889 A1 | | 6/2008 |
| EP | 1 917 254 | | 12/2008 |
| WO | WO 2007/000628 | | 1/2007 |
| WO | WO 2007012984 A2 | * | 2/2007 |
| WO | WO 2008074887 A1 | * | 6/2008 |

OTHER PUBLICATIONS

"The role of the column in preparative HPLC." Column Watch, ed. Majors, R. E., May 2004, 22(5), 416-428. [online][retrieved on Mar. 8, 2013] Retrieved from the Internet: <http://www.pharmtech.com/pharmtech/data/articlestandard/lcgc/252004/99401/article.pdf.*

Takatori, S. et al. "A rapid and easy multiresidue method for the determination of pesticide residues in vegetables, fruits, and cereals using liquid chromatography/tandem mass spectrometry." J. AOAC Int. 2008, 91, 871-883.*

International Search Report, Jun. 9, 2010.

Written Opinion of the International Searching Authority, Jun. 9, 2010.

* cited by examiner

*Primary Examiner* — Samantha Shterengarts
*Assistant Examiner* — Amanda L Aguirre
(74) *Attorney, Agent, or Firm* — Abelman, Frayne & Schwab

(57) ABSTRACT

The present invention relates to a process for the purification of amorolfine hydrochloride by means of a reversed-phase preparative high performances liquid chromatography (prep-HPLC) said method starting from a crude Amorolfine hydrochloride having purity higher than 90% and containing Bepromoline hydrochloride <5% and Fenpropimorf <3%. The process involves the use of a mobile phase comprising water and an organic solvent under isocratic conditions.

10 Claims, 4 Drawing Sheets

| Peak # | RetTime [min] | Type | Width [min] | Area mAU *s | Height [mAU ] | Area % |
|---|---|---|---|---|---|---|
| 1 | 4.493 | MM | 0.1678 | 1919.13623 | 190.59145 | 3.8692 |
| 2 | 10.201 | MM | 0.3579 | 1168.46057 | 54.40843 | 2.3557 |
| 3 | 12.609 | MF | 0.2898 | 749.34607 | 43.10089 | 1.5108 |
| 4 | 13.260 | FM | 0.5456 | 4.49941e4 | 1374.44812 | 90.7133 |
| 5 | 17.855 | MF | 0.6783 | 580.53467 | 14.26429 | 1.1704 |
| 6 | 19.229 | FM | 0.6243 | 188.76053 | 5.03918 | 0.3806 |
| Totals : | | | | 4.96004e4 | 1681.85236 | |

| Product | Retention time (min) |
|---|---|
| Bepromoline | 4.493 |
| Fenpropimorph | 10.201 |
| Amorolfine | 13.260 |

Detector A Ch1 210nm

| Peak# | Ret. Time | Area | Height | Area % |
|---|---|---|---|---|
| 1 | 3.776 | 15110675 | 401422 | 3.424 |
| 2 | 11.266 | 7453738 | 160066 | 1.689 |
| 3 | 12.353 | 3074562 | 66341 | 0.697 |
| 4 | 14.785 | 413216281 | 2272782 | 93.624 |
| 5 | 29.962 | 2503874 | 17564 | 0.567 |
| Total | | 441359130 | 2918174 | 100.000 |

| Product | Retention time (min) |
|---|---|
| Bepromoline | 3.615 |
| Fenpropimorph | 11.202 |
| Amorolfine | 15.013 |

| Peak # | RetTime [min] | Type | Width [min] | Area mAU *s | Height [mAU ] | Area % |
|---|---|---|---|---|---|---|
| 1 | 9.861 | MM | 0.8696 | 10.18418 | 1.95185e-1 | 0.0350 |
| 2 | 12.702 | MM | 0.4750 | 2.90762e4 | 1020.31372 | 99.9162 |
| 3 | 17.859 | MM | 0.3473 | 14.19192 | 4.85948e-1 | 0.0488 |
| Totals : | | | | 2.91006e4 | 1020.99485 | |

| Product | Retention time (min) |
|---|---|
| Fenpropimorph | 9.861 |
| Amorolfine | 12.702 |

PROCESS FOR THE PREPARATION AND PURIFICATION OF AMOROLFINE HYDROCHLORIDE

RELATED CASES AND PRIORITY CLAIM

Applicant claims priority under 35 U.S.C. Sections 119. 120 and/or 365 on PCT/EP2010/U52047 having International Filing Date 18 Feb. 2010 and FI2009A000032 having filing date 20 Feb. 2009.

FIELD OF THE INVENTION

The present invention refers to the field of industrial production processes, and in particular to a process for the industrial production of amorolfine hydrochloride.

STATE OF THE ART

Amorolfine hydrochloride (AMF.HCl), a compound of formula (I), is a pharmaceutical active ingredient with a fungicidal action used in topical preparations with antimycotic properties.

(I)

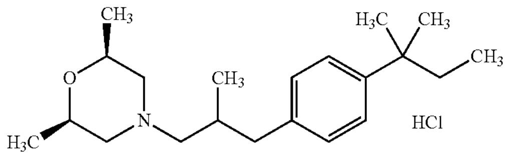

Amorolfine HCl

EP0024334 B1 describes a method for producing the amorolfine base (AMF base) that is a compound with a structural formula (II):

(II)

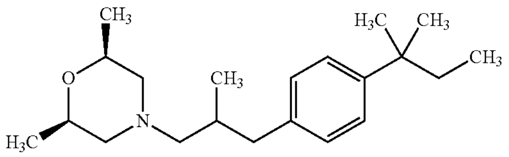

Amorolfine
free base said method includes a step in which bepromoline (BPM), a compound of formula (III):

(III)

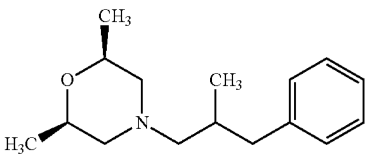

Bepromoline is made to react with 2-methyl-2-butanol in a Friedel-Crafts alkylation to form the crude amorolfine base.

The Friedel-Crafts reaction is obtained using concentrated sulphuric acid as the catalyst.

In detail, concentrated sulphuric acid is added to bepromoline in dichloromethane at −5° C., then 2-methyl-2-butanol is added. The reaction temperature is not considered a crucial parameter but it is recommended that it be kept between 0 and 50° C., and preferably 18-20° C. The solution is then treated with water and the aqueous phase is extracted several times with dichloromethane. Then the organic phases are washed with sodium hydroxide and water and, after drying, evaporation of the solvent produces the crude amorolfine base, in the form of an oily substance that is purified by low-pressure distillation with a boiling point at 120° C./0.1 mbar.

WO2007012983 describes a variation of the production method described in EP0024334. The process described in WO2007012983 involves treating a bepromoline hydrochloride solution in dichloromethane by adding iron trichloride at room temperature, followed by cooling to a temperature ranging between −40 and −60° C., and preferably −50° C., and the subsequent addition of 2-chloro-2-methylbutane.

This method enables the crude amorolfine base to be obtained with a yield of approximately 90% and with a content of impurities that makes purification by distillation essential. In particular, the reaction is conducted at −50° C. to reduce the formation of the fenpropimorph by-product, which is difficult to remove from the end-product. To limit the formation of fenpropimorph, it is advisable to use 2-chloro-2-methylbutane in proportions of 1:1 with respect to the starting bepromoline. The reaction work-up involves washing the organic phase with a solution of sodium phosphate and then with a solution of sodium hydroxide; said washing steps are then followed by a solvent exchange from dichloromethane to toluene and subsequent extraction with water. After evaporating the toluene, the crude amorolfine base needs to be distilled at low pressure (0.14-0.15 mbar) at 141-144° C. to obtain a sufficiently pure product. The above-described work-up is considered necessary in order to be able to perform the distillation step on an industrial scale.

There is subsequently a description of how the amorolfine hydrochloride is formed by the addition of gaseous hydrochloric acid and a crystallisation in ethanol to reduce the content of impurities in the end-product.

At the state of the art, in processes for the production of AMF.HCl for pharmaceutical use, the purification need to be performed at the AMF base stage and the only efficient methodology is the reduce pressure distillation step whose operation, at bulk scale, is difficult to be handled. At AMF.HCl stage the crystallization procedures do not allow to remove efficiently BPM or FPM eventually present and therefore pure AMF.HCl can be obtained only starting from an AMF base already enough pure. It is therefore evident the need of an alternative purification method in the production process of AMF.HCl.

The object of the invention is to provide a method for purifying the amorolfine hydrochloride, in particular a method applicable on an industrial scale that could allow, amorolfine hydrochloride to be obtained with an economically advantageous yield and a purity suitable for use in pharmaceutical preparations.

Further problem at the state of the art is that the best known synthetic processes require the bepromoline alkylation to be performed at very low temperatures, for controlling by-product formation, and require tedious and costly work-up operations. Is therefore evident the need of an improved synthetic process that at least could make it unnecessary to distil the amorolfine base, and wherein the bepromoline alkylation could be done at temperatures no lower than −20° C.

DEFINITIONS AND ABBREVIATIONS

AMF base: amorolfine base

AMF.HCl: amorolfine hydrochloride

BPM: bepromoline
FPM: fenpropimorph
Area %: unit of purity calculated using an analytical chromatogram. It is the area of the component required divided by the total area considered.
Charge ratio: the mass of the stationary phase divided by the mass of the product charged in the column for a chromatographic run.
Mobile phase: the liquid pumped through the column after charging the product. This liquid elutes the components of the product.
Stationary phase: the medium that adsorbs the components charged in the column.
Yield: the mass of the required component collected in the purified fractions divided by the mass of the product charged in the column.

SUMMARY OF THE INVENTION

The present invention relates to a method for purifying crude amorolfine hydrochloride by reverse-phase preparative high-performances liquid chromatography (prep-HPLC). Said prep-HPLC method starting from a crude amorolfine hydrochloride having an analytical HPLC purity grade higher than 90%, with a bepromoline hydrochloride content of less than 5% and a fenpropimorph hydrochloride content below 3%. The prep-HPLC method allows to obtain a pure amorolfine hydrochloride product having an analytical HPLC purity grade higher than 99.5% with a content of impurities Bepromoline, Fenpropimorf and other detected impurities each ones below 0.1 wt %

The inventors of the present patent application have further discovered that significant synergistic benefits, in terms of yield and product purity, can be obtained if said crude amorolfine hydrochloride is prepared by means of a synthetic process comprising:

I. the preparation of a crude amorolfine base by means of bepromoline hydrochloride alkylation with:
   - 2-chloro-2-methylbutane using a Friedel-Crafts catalyst chosen from the $FeCl_3$ or $AlCl_3$ group; or
   - 2-methyl-2-butanol using concentrated sulphuric acid as the Friedel-Crafts catalyst;

said alkylation being characterised in that it is performed at a temperature T that is higher than −20° C. and lower than a 0° C.;
II. the preparation of a crude amorolfine hydrochloride from the crude amorolfine base, as obtained after the Friedel-Crafts alkylation (I), said preparation comprising a treatment with HCl.

Subject of the present invention is therefore also a process for the production of Amorolfine HCl, said process comprising the prep-HPLC method as above described.

Further subject of the present invention is a synthetic process for the preparation of a crude Amorolfine HCl, having an analytical HPLC purity grade higher than 90%, with a bepromoline hydrochloride content of less than 5% and a fenpropimorph hydrochloride content below 3%, therefore particularly suitable for being purified by means of the prep-HPLC method as above described, said synthetic method comprising steps (I) and (II) as above described.

DETAILED DESCRIPTION OF THE INVENTION

Regarding the synthetic process for preparing crude amorolfine hydrochloride, according to the invention said process comprises a step (I) for preparing a crude amorolfine base by means of a Friedel-Crafts alkylation of bepromoline hydrochloride that is preferably performed by means of the following detailed steps:

(a) bepromoline hydrochloride, a compound of formula (III), is added to a solution of $FeCl_3$ or $AlCl_3$, preferably $FeCl_3$, in an aprotic solvent at a temperature in the range of 20 to 40° C.;
(b) 2-chloro-2-methylbutane is added to the mixture obtained from step (a), at a temperature T;

or:

(a') concentrated sulphuric acid is added to a solution of bepromoline hydrochloride, a compound of formula (III), in an aprotic solvent at a temperature in the range of −10 to −0° C.;
(b') 2-methyl-2-butanol is added to the mixture obtained from step (a'), at a temperature T.

After said steps (b) or (b'):

(c) the temperature T is maintained for the time it takes to complete the alkylation reaction;

said Friedel-Crafts alkylation being characterised in that the temperature T is higher than −20° C. and lower than 0° C.

Preferably said process comprises a step (II) for preparing a crude amorolfine hydrochloride from the crude amorolfine base, as obtained from the above described step (I), that is preferably conducted by means of the following detailed steps:

(h) the crude amorolfine base is dissolved in isopropyl alcohol and gaseous hydrochloric acid is added;
(i) the crude amorolfine hydrochloride is crystallised in isopropyl alcohol;
(j) the crude amorolfine hydrochloride is purified by reverse-phase preparative high-pressure chromatography (prep-HPLC) method according to the main subject of the invention.

In a preferred embodiment of the present invention therefore the prep-HPLC method is step (j) of an overall process which includes the above described synthetic process.

In a preferred case, after step (c) and before step (II), the reaction mixture is worked up by means of the following steps to complete the alkylation reaction:

(d) water is added to the reaction mixture coming from step (c) while the temperature is maintained below 10° C.;
(e) the organic phase is separated (preferably with methylene chloride);

(f) the organic phase is washed with a basic aqueous solution (e.g. a solution of sodium hydroxide) and then the organic phase is separated;

(g) the solvent is removed from the organic phase (e.g. methylene chloride) by distillation and the crude amorolfine base is isolated as an oily substance.

Figure 1:
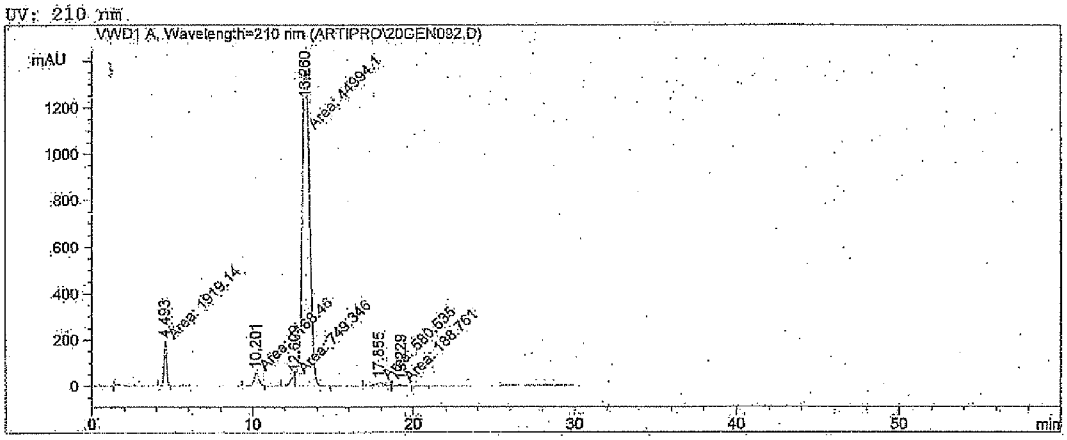
FIG. 1—Chromatogram of the crude amorolfine hydrochloride obtained by means of the synthetic process according to the present invention, before purification by reverse-phase prep-HPLC.

The above described synthetic process, after crystallisation in isopropyl alcohol, results in a crude amorolfine hydrochloride having an analytical HPLC purity grade higher than 90%, with a bepromoline hydrochloride content of less than 5% and a fenpropimorph hydrochloride content below 3% (as shown in FIG. 1).

Such low amount of the known impurities is surprising, especially when Friedel-Crafts is performed using 2-chloro-2-methylbutane as starting material, since performing the alkylation at temperatures not lower than −20° C. the skilled in the art, from prior art teachings, would expect to find higher levels of FPM impurity. Furthermore it has been found that such a crude Amorolfine is particularly suitable for being efficiently purified by means of the prep-HPLC method according to the present invention, thus avoiding the tedious and costly distillation of the crude AMF base.

One further advantage of the above-described process lies in that it enables amorolfine hydrochloride with a high purity grade (>90%) to be obtained, avoiding the need to distil the crude amorolfine base. Another advantage lies in the use of reaction temperatures no lower than −20° C. for the Friedel-Crafts alkylation.

For the purposes of the present invention, the term aprotic solvent is used to mean an inert organic solvent, e.g. hexane, cyclohexane, chloroform, dichloromethane or dichloroethane; dichloromethane is preferred.

In a preferred case, step (a) is completed using molar quantities of catalyst in the range of 1.1 to 1.2 with respect to the bepromoline hydrochloride.

In a preferred case, step (a') is completed using molar quantities of catalyst in the range of 11 to 12 with respect to the bepromoline hydrochloride.

In a preferred case, step (b) is completed using molar quantities of 2-chloro-2-methylbutane in the range of 1.1 to 1.3 with respect to the bepromoline hydrochloride.

In a preferred case, step (b') is completed using molar quantities of 2-methyl-2-butanol in the range of 1.9 to 2.1 with respect to the bepromoline hydrochloride.

On completion of the alkylation reaction, step (c) can be monitored by means of methods known to a person skilled in the art.

According to a first aspect of the invention, a preparative reverse-phase preparative high-performance liquid chromatography (prep-HPLC) method is described for purifying the compound with the formula (I), namely a crude amorolfine hydrochloride (with an analytical HPLC purity higher than 90%) obtaining a product with a content of bepromoline, fenpropimorph and other identified impurities of less than 0.1 wt % (for each impurity).

The prep-HPLC method can be used for Crude Amorolfine HCl synthesised by means of known synthetic processes in so far these provide a crude Amorolfine HCl of a purity as above described. Known synthetic procedure if performed as disclosed provide an end product which is enough pure for pharmaceutical use, but if a batch processing was failed due to some issues, the prep-HPLC of the invention can be used as recovery procedure. To be noticed that if a process known in the art is performed as disclosed but just omitting the distillation step of the crude AMF base, it would provide a crude Amorolfine HCl with a purity <90% or a content of impurities higher to that suitable for the prep-HPLC purification. It was instead observed that combining the above described synthetic process with the prep-HPLC method the overall process bring advantageous effects in terms of purity of the end product, simplicity of operations (solvent exchanges are not needed and low pressure distillation of AMF base is avoided), energy saving, cost efficiency and process robustness.

In a particularly preferred embodiment therefore the crude amorolfine hydrochloride is obtained by the above-described synthetic process up to step (i), and is purified by means of the prep-HPLC method, step (j), according to the present invention.

The prep-HPLC method is accomplished using an reverse phase as the stationary phase. By collecting a series of fractions, which are partially recycled, amorolfine hydrochloride with a high purity grade is eluted from the column and obtained with a high yield. The amorolfine hydrochloride produced according to the present prep-HPLC method has a content of bepromoline, fenpropimorph and other identified impurities of less than 0.1 wt % (each impurity).

According to the present invention, the crude amorolfine hydrochloride with a higher than 90% purity is dissolved in a mixture of water or acidic water and a polar organic solvent. Preferably for the dissolution mixture is used just water, sometimes it is necessary to use acidic water to accomplished complete dissolution and guarantee the Amorolfine HCl is in its salt form. The concentration of the amorolfine hydrochloride in the solution is normally in the range of 20 g/l to 200 g/l, and preferably 70-80 g/l.

The prep-HPLC method of the invention make use of a mobile phase which is a mixture of water or acidic water and a polar water-miscible organic solvent, wherein the amount of organic solvent in the mobile phase is comprised in the range 5-95 wt %, preferably 50-90 wt % more preferably 70-90 wt % in case of acidic water or 60-80 in case of just water.

The polar organic solvent may be any water-miscible solvent, e.g. acetonitrile, methanol, propanol, isopropanol, butanol, t-butanol, and is preferably methanol. Preferably in the mobile phase is used just water, sometimes it is necessary to use acidic water. The acids used to acidify the amorolfine hydrochloride solution and the acidic mobile phase include inorganic acids such as hydrochloric acid, hydrobromic acid, phosphoric acid, nitric acid, and sulphuric acid. Organic acids may also be used, such as acetic acid, formic acid, oxalic acid, succinic acid, lactic acid, and tartaric acid. The quantity of acid added must be sufficient to lower the pH of the solution to a level in the range of 2 to 7.5, and preferably from 4 to 6. An acetic acid and ammonium, sodium or potassium acetate buffer is preferred. Preferred mobile phases for C18 stationary phases are mixtures MeOH/water=60/40 or MeOH/acidic water=70/30.

The quantity of acid added must guarantee the presence of the amorolfine hydrochloride in the form of a salt in the solution charged in the column. This is because it has been observed that the amorolfine base is retained strongly by the stationary phase of the column, so the amorolfine hydrochloride solution must be suitably acidified to ensure the recovery of the amorolfine hydrochloride with the limited volumes of eluent contained in the column.

The stationary phase can consist of various materials, such as alkyl silanes, aryl silanes, haloalkyl silanes, alkyl esters, alkyl amines, alkyl cyan compounds, alkyl diols, alkyl ethers, aryl ethers, haloalkyl ethers, alkyl carboxylic acids, aryl carboxylic acids, alkyl sulfonic acids, aryl sulfonic acids, polystyrene divinylbenzene, amino polycaprolactam, and glycidol ethyl methoxysilane. The stationary phase typically used is silica with alkyl ligands having 4 (C4), 8 (C8), and preferably 18 (C18) carbon atoms. The ligands can be attached to other particles, such as polymers, zircon oxide or titanium. The stationary phase consists of spherical particles with a diameter of 10-20 μm and a pore diameter of 60-120 Angstroms. Particularly preferred stationary phases are SepTech-ST60 10 μm RP18, Purospher STAR RP-18-e (10 μm), C18 Daisogel (10 um, 100 Å), C18 Kromasil (10 um, 100 Å), C18 Luna (10 um, 100 Å).

A high-performance chromatographic column is used with an internal diameter greater than 5 cm and a length in the range of 5 to 100 cm, and preferably between 20 and 30 cm.

The chromatographic separation is achieved by maintaining the temperature in a range of 10 to 40° C., and preferably 20-30° C.

The amorolfine hydrochloride and its impurities become distributed between the stationary phase and the mobile phase and are eluted from the mobile phase consisting of an (optionally acidic) aqueous solution and an organic solvent.

When the aqueous solution is acidic is buffered and is preferably prepared by adding a quantity of acetic acid and ammonium acetate sufficient to adjust the pH to between 4 and 6.

The charge ratio used in the prep-HPLC method is in the range of 70 to 130 grams of stationary phase per gram of amorolfine hydrochloride charged in the column before elution with the mobile phase.

Operatively, after charging the column with the solution of crude amorolfine hydrochloride, each component (impurities and amorolfine hydrochloride) is eluted in isocratic conditions with the mobile phase containing a quantity of methanol in the range of 50 to 90 wt %.

The fractions are collected in correspondence to the elution of the components of the mixture of crude amorolfine and its impurities, i.e. in line with the corresponding UV absorption peaks at 210 nm (as shown in FIG. 2). Several fractions are collected, those containing only purified Amorolfine HCl are pooled together, those containing also small amounts of impurities are reprocessed onto the column.

In case the mobile phase comprises acidic buffered water, prep-HPLC (step (j)), which provides buffered aqueous fractions containing amorolfine hydrochloride, is followed by the steps described below:

(k) the aqueous fractions containing the purified amorolfine hydrochloride are evaporated to completely eliminate the organic solvent (e.g. methanol) contained in the mobile phase;

(l) a base (e.g. sodium hydroxide) is added to the resulting aqueous solution until a pH=12 is obtained and the amorolfine base thus obtained is extracted with a water-immiscible organic solvent (e.g. methylene chloride) to obtain an oily product corresponding to a purified amorolfine base;

(m) the purified amorolfine base is dissolved in isopropyl alcohol and gaseous hydrochloric acid is added to the solution, with the precipitation of the amorolfine HCl that is then crystallised in isopropyl alcohol, obtaining a product with a high purity grade.

Preferably according to the invention the mobile phase used in the prep-HPLC method is free of acidic salts or buffers and in this case the fractions eluted from the column containing the purified AMF HCl are simply pooled and after solvent evaporation the AMF HCl is crystallised, preferably from isopropyl alcohol. Preferably, according to the present prep-HPLC method, the eluate from the column corresponding to the Amorolfine HCl peak is divided in a plurality fractions which are all collected (as example see FIG. 2B). Those fractions which contains only the purified Amorolfine HCl are pooled, those which contains impurities are pooled apart and reprocessed in the column then those reprocessed fractions which contains only the purified Amorolfine HCl are pooled together with the first ones.

The prep-HPLC method of the invention provides an high grade (>99.5% purity) Amorolfine HCl which is suitable for pharmaceutical use.

Further subject-matter of the present invention is a process for the production of Amorolfine HCl for pharmaceutical use, said process comprising the prep-HPLC method as above described.

The present invention may be further clarified by means of the following practical examples.

EXPERIMENTAL PART

Example 1

Preparation of the Amorolfine Base with Iron Chloride as the Friedel-Crafts Catalyst Amorolfine base is produced by making bepromoline hydrochloride react with 2-chloro-2-methyl butane in methylene chloride using iron chloride as the Friedel-Crafts catalyst and maintaining the temperature at −20° C.

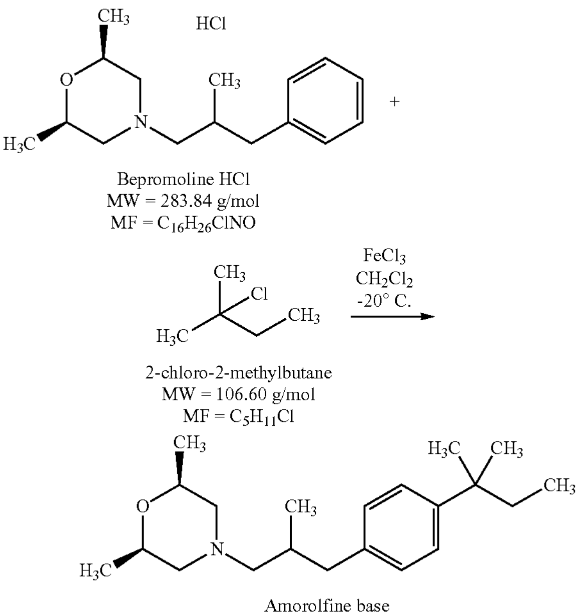

Bepromoline HCl
MW = 283.84 g/mol
MF = $C_{16}H_{26}ClNO$ 2-chloro-2-methylbutane
MW = 106.60 g/mol
MF = $C_5H_{11}Cl$ Amorolfine base
MW = 317.52 g/mol
MF = $C_{21}H_{35}NO$ A reactor is loaded with 9.5 mmol of iron chloride and 4 ml of methylene chloride. The resulting mixture is heated to 30° C., then 6 ml of a methylene chloride solution containing 8.35 mmol of bepromoline hydrochloride are added drop by drop. The mixture is subsequently stirred for 10 minutes, maintaining the temperature at 33° C. approx., then it is cooled to −20°

C. Two ml of a methylene chloride solution containing 10.04 mmol of 2-chloro-2-methylbutane are added to the mixture drop by drop. The reaction mixture is stirred for 2.5 hours, maintaining the temperature at −20° C., then 6 ml of water are added and the temperature is maintained below 10° C. The aqueous phase is eliminated and the organic phase is washed with 6 ml of water. Twelve ml of water are added to the organic phase together with a quantity of 10% sodium hydroxide aqueous solution sufficient to adjust the pH to 10-12. The organic phase is separated and the aqueous phase is extracted again with 12 ml of methylene chloride. The organic phase is distilled until the methylene chloride has been completely removed, obtaining 2.6 g of amorolfine base in the form of an oily substance.

Example 2

Preparation of the Amorolfine Base with Aluminium Chloride as the Friedel-Crafts Catalyst Amorolfine base is produced by making bepromoline hydrochloride react with 2-chloro-2-methyl butane in methylene chloride using aluminium chloride as the Friedel-Crafts catalyst and maintaining the temperature at −10° C.

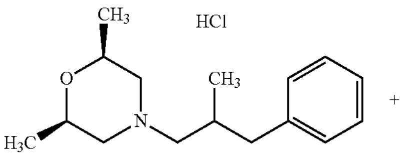

Bepromoline HCl
MW = 283.84 g/mol
MF = $C_{16}H_{26}ClNO$

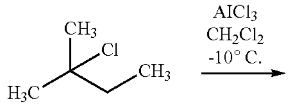

2-chloro-2-methylbutane
MW = 106.60 g/mol
MF = $C_5H_{11}Cl$

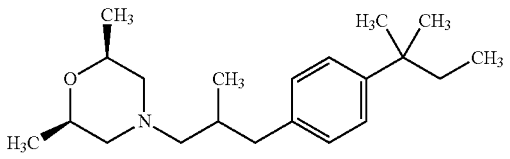

Amorolfine base
MW = 317.52 g/mol
MF = $C_{21}H_{35}NO$

A reactor is loaded with 9.5 mmol of aluminium chloride and 4 ml of methylene chloride. The resulting mixture is heated to 30° C., then 6 ml of a methylene chloride solution containing 8.35 mmol of bepromoline hydrochloride are added drop by drop. The mixture is subsequently stirred for 10 minutes, maintaining the temperature at 35° C. approx., then it is cooled to −10° C. Two ml of a methylene chloride solution containing 10.04 mmol of 2-chloro-2-methylbutane are added to the mixture drop by drop. The reaction mixture is stirred for 2.5 hours, maintaining the temperature at −10° C., then 10 ml of water are added and the temperature is maintained below 10° C. The aqueous phase is eliminated and the organic phase is washed with 10 ml of water. Twelve ml of water are added to the organic phase together with a quantity of 10% sodium hydroxide aqueous solution sufficient to adjust the pH to 10-12. The organic phase is separated and the aqueous phase is extracted again with 12 ml of methylene chloride. The organic phase is distilled until the methylene chloride has been completely removed, obtaining 2.5 g of amorolfine base in the form an oily substance.

Example 3

Preparation of the Amorolfine Base with Sulphuric Acid as the Friedel-Crafts Catalyst Amorolfine base is produced by making bepromoline hydrochloride react with 2-methyl-2-butanol in methylene chloride using sulphuric acid as the Friedel-Crafts catalyst, and maintaining the temperature at −5° C.:

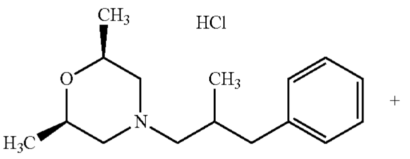

Bepromoline HCl
MW = 283.84 g/mol
MF = $C_{16}H_{26}ClNO$

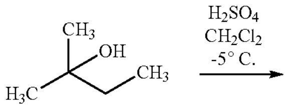

2-methyl-2-butanol
MW = 88.15 g/mol
MF = $C_5H_{12}O$

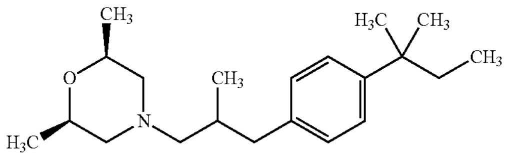

Amorolfine base
MW = 317.52 g/mol
MF = $C_{21}H_{35}NO$

A reactor is loaded with 11.06 mmol of bepromoline hydrochloride and 18 ml of methylene chloride. The resulting mixture is cooled to −5° C., then 129.7 mmol of 96% sulphuric acid are added to the mixture drop by drop. Six ml of a methylene chloride solution containing 22.12 mmol of 2-methyl-2-butanol are subsequently added drop by drop, maintaining the temperature at −5° C. The reaction mixture is stirred for 1 hour, maintaining the temperature at −5° C., then 25 ml of water are added, maintaining the temperature below 10° C. The aqueous phase is eliminated and the organic phase is washed with 25 ml of water. Twenty ml of water are added to the organic phase together with a quantity of 10% sodium hydroxide aqueous solution sufficient to adjust the pH to 10-12. The organic phase is separated and the aqueous phase is extracted again with 20 ml of methylene chloride. The organic phase is distilled until the methylene chloride has been completely removed, obtaining 2.5 g of amorolfine base in the form of an oily substance.

Example 4

Formation and Crystallisation of Crude Amorolfine Hydrochloride with a Purity Grade >90%

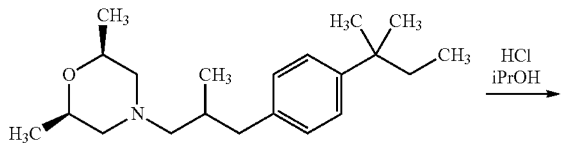

Amorolfine base
MW = 317.52 g/mol
MF = $C_{21}H_{35}NO$

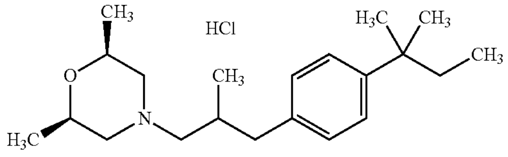

Amorolfine HCl
MW = 353.98 g/mol
MF = $C_{21}H_{36}ClNO$

A reactor is loaded with 2.6 g of amorolfine base (as obtained by means of any of the previous Examples 1-3) dissolved in 10.5 ml of isopropanol; gaseous hydrochloric acid is bubbled through the solution and the crude amorolfine hydrochloride precipitates. The amorolfine hydrochloride is crystallised in the same reactor, without isolating the product and without adding any other solvent, by heating the suspension until it has dissolved completely, then cooling it to 15-30° C. until crystals form. The mixture is stirred at 15-30° C. for 2 hours. After filtering and drying, 2.8 g of crude amorolfine hydrochloride are obtained with a analytical HPLC purity grade >90% and with a bepromoline hydrochloride content <5% and a fenpropimorph hydrochloride content <3% (as shown in FIG. 1).

Example 5

Preparative HPLC Purification of the Crude Amorolfine Hydrochloride

Crystallized crude amorolfine HCl, as obtained from example 4, is purified by preparative high performance liquid chromatography (HPLC). The chromatographic process is accomplished in a Shimadzu chromatographic system comprising:

an LC-8A pump for liquid chromatography
a Vis SPD-10Avp UV detector
a FRC-10A fraction collector
a CBM-20° system controller
LC Solution software The chromatographic parameters are as follows:

stationary phase: Purospher STAR RP-18-e (10 μm), with an internal diameter of 2.5 cm and a length of 25 cm
mobile phase: 30% aqueous solution (1% ammonium acetate+3% acetic acid)−70% methanol
pH of the buffered solution=4.1
flow rate in the column: 30 ml/min
detector (wavelength): 210 nm
sample: 300 mg of crude amorolfine hydrochloride in 5 ml of mobile phase
loop volume: 5 ml
number of runs: 6

Figure 2A:
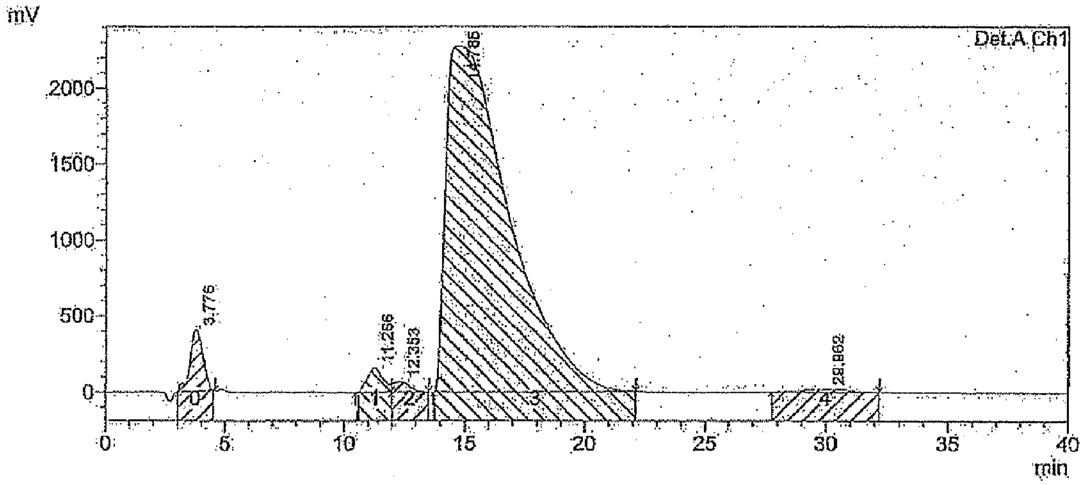
FIG. 2A—Chromatogram of the prep-HPLC method of the invention, as described in example 5, showing the main peaks and the corresponding fractions isolated by collecting the eluted mobile phase when the absorbance at 210 nm is higher than 1% of the main peak of the fraction.

In a flask, 1.8 g of 90% crude amorolfine hydrochloride are dissolved in 30 ml of mobile phase. After charging 5 ml of the amorolfine hydrochloride solution in the column, each component is eluted in isocratic conditions with the mobile phase and the corresponding fractions are collected at the time of elution of the various components of the mixture being purified, i.e. in line with their respective UV absorption peaks at 210 nm (as shown in FIG. 2A).

The first fraction eluted (indicated as fraction 0 in FIG. 2A) contains the bepromoline hydrochloride impurity, the second fraction (indicated in FIG. 2A as fraction 1) contains the fenpropimorph hydrochloride impurity, and the third fraction (indicated in FIG. 2A as fraction 2) contains a small amount of amorolfine hydrochloride and the remainder of the fenpropimorph hydrochloride, the fourth fraction (indicated in FIG. 2A as fraction 3) contains the purified amorolfine hydrochloride and, finally, the fifth fraction (indicated in FIG. 2A as fraction 4) contains unidentified impurities. A sixth fraction is collected by eluting the column with a mobile phase containing approximately 90% of organic solvent (e.g. methanol) to eliminate the remaining amount of the charged crude amorolfine hydrochloride. This sixth fraction is combined with the third fraction, evaporated and reprocessed in the column. The eluate containing the purified product is combined with the fourth fraction. The combined fractions containing the purified amorolfine hydrochloride are evaporated to completely eliminate the methanol. The residue is diluted with 100 ml of water and 100 ml of methylene chloride. Sodium hydroxide is added to the mixture to adjust the pH to 12. The organic phase is separated and the aqueous phase is extracted again with 50 ml of dichloromethane. The organic phases are combined and the methylene chloride is removed by distillation, obtaining 1.2 g of amorolfine base in the form of an oily substance.

These 1.2 g of amorolfine base are dissolved in 5 ml of isopropyl alcohol and gaseous hydrochloric acid is added to the solution with the precipitation of the amorolfine HCl that is then crystallised in isopropyl alcohol, obtaining a product with a high purity grade. The same reactor is used, without isolating the product and without adding any other solvent, to crystallise the amorolfine hydrochloride by heating the suspension until it has dissolved completely, then cooling to 15-30° C. until crystals form. The mixture is stirred at 15-30° C. for 2 hours.

Figure 3:
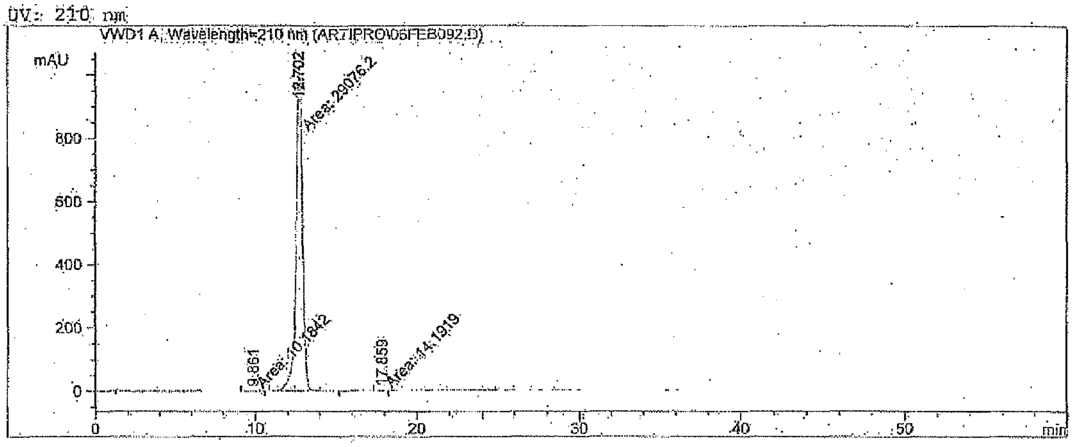
FIG. 3—Analytical chromatogram of the amorolfine hydrochloride obtained by means of the process according to the present invention, after purification by reverse-phase HPLC.

After filtering and drying, 1 g of amorolfine hydrochloride is obtained with a analytical HPLC purity >99.8% and with a bepromoline hydrochloride content <0.1%, a fenpropimorph hydrochloride content <0.1% and a content of all the other impurities identified <0.1% (as shown in FIG. 3).

Example 6

Preparative HPLC Purification of the Crude Amorolfine Hydrochloride

Figure 2B:
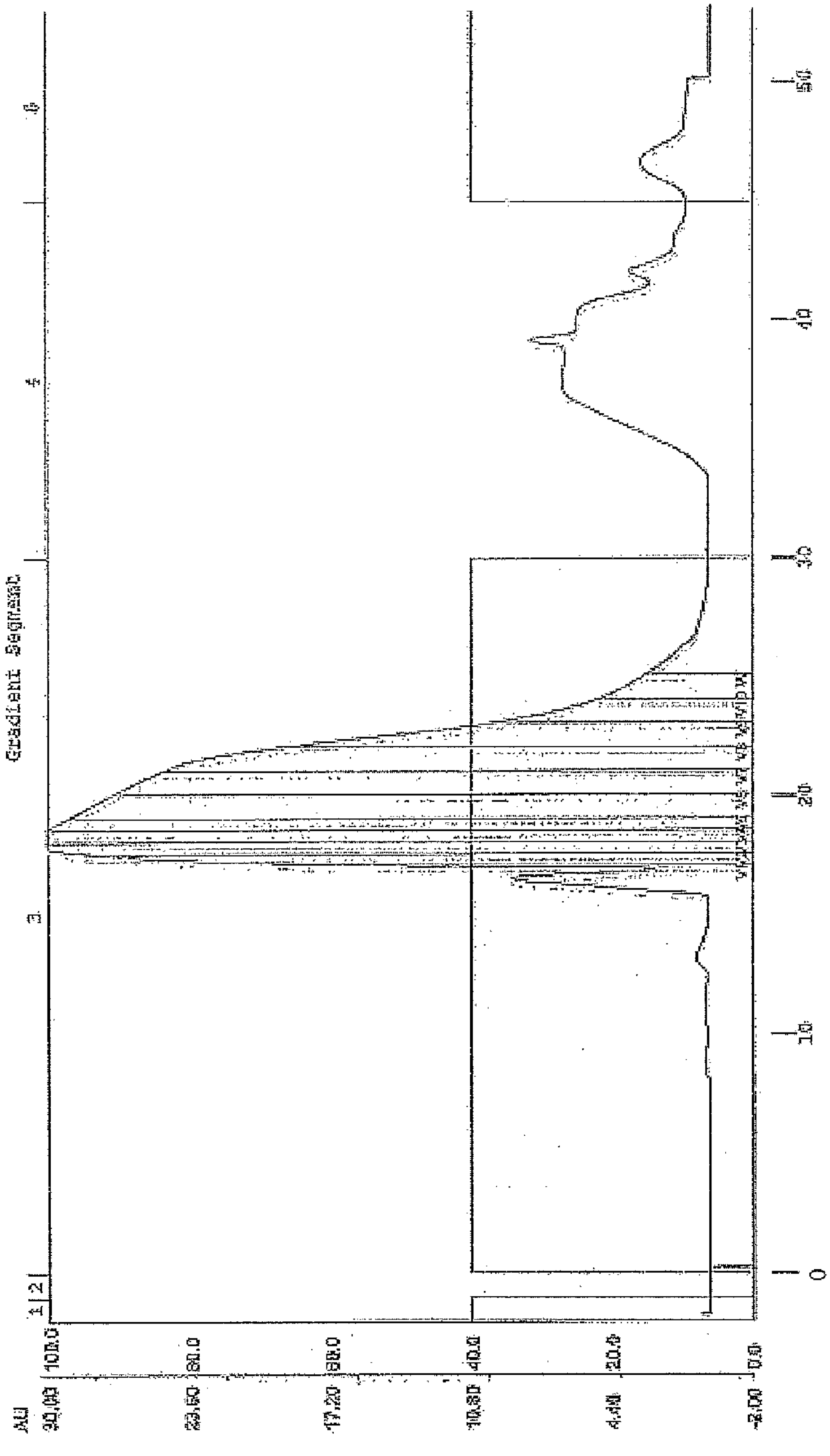
FIG. 2B—Chromatogram of the prep-HPLC method of the invention, as described in example 6, showing the main peak of AMF.HCl and the corresponding fractions isolated by collecting the eluted mobile phase when the absorbance at 210 nm is higher than 1% of the main peak.

Crystallized crude amorolfine HCl, as obtained from example 4, is purified by preparative high performance liquid chromatography (HPLC), the equipment used is the PrepLC system Varian, the component are following listed:

PrepStar 530 Control Module (model OPTO Control 00150)
PrepStar 530 Fluidics Module (model 530 Fluidics 00100)
Solvent Delivery Module (model SD2B and SD 2A)
Detector Prostar (model 325 EL06069028)
Inject Pump (Prostar 218 01096)
Stationary Phase:
SepTech-ST60 10 μm RP18. (or equivalent)
Injection Volume: 150 ml Mobile Phase:
60% [MeOH]: 40% [$H_2O$]
Flow: 200 ml/min.
Detector: 225 nm
Sample:
crude Amorolfine HCl (batch code I057AA00) dissolved in 70% [MeOH]: 30% [$H_2O$] solution in order to obtain a 0.2 g/ml solution.
Procedure:

Sample solution is loaded on column (the volume of each cycle is of 150 ml of the 0.2 g/ml sample solution) and eluted with mobile phase. For each cycle ten fractions are collected, as indicated in FIG. 2B.

Fractions num 1,2 and 10 are reprocessed. An IPC is performed on the fractions 3,4, 8 and 9; if suitable these are collected with the fractions 5, 6 and 7, if not these must be reprocessed with the num 1,2 and 10.

The reprocess of the collected fractions is performed by evaporation, the residue is suspended in isopropyl alcohol, isolated by filtration and dried. The dried product is then dissolved in 70% [MeOH]: 30% [$H_2O$] solution in order to obtain a 0.2 g/ml solution and purified by HPLC (the total volume is divided in cycles of 150 ml each) for each cycle the only fractions 3-9 are collected (the fractions num 3,4,8 and 9 are collected after IPC control). The fractions 1,2 and 10 are sent to the waste.

Fractions containing the purified product are collected, the solvent is distilled off and to the residue isopropyl alcohol (2.4 l) is added, the reaction mass is dissolved by heating at about 55-65° C.; cool down the reaction mass at 30-35° C. maintaining the temperature for about 2 h; then cool down at 20-25° C. maintaining the temperature for about 3 h.

The isolated purified Amorolfine is filtered washing the product on the filter with isopropyl alcohol; The isolated product is dried at 50° C. for about 9 h till LOD NMT 0.5%.

After filtering and drying, amorolfine hydrochloride is obtained with a analytical HPLC purity >99.8% and with a bepromoline hydrochloride content <0.1%, a fenpropimorph hydrochloride content <0.1% and a content of all the other impurities identified <0.1% (as shown in FIG. 3).

The invention claimed is:

1. A process for the synthetic preparation of a crude Amorolfine hydrochloride having purity higher than 90% and containing <5% Bepromoline hydrochloride and <3% Fenpropimorf, comprising:

I. preparing Amorolfine base by alkylating Bepromoline with:
   2-chloro-2-methylbutane in presence of a Friedel-Crafts catalyst selected from the group consisting of $FeCl_3$ and $AlCl_3$; or
   2-methyl-2-butanol in presence of concentrated sulphuric acid as Friedel-Crafts catalyst;
   at a temperature T higher than −20° C. and lower than 0° C.; and II. preparing crude Amorolfine hydrochloride from the Amorolfine base prepared in I, by treating said Amorolfine base with hydrochloric acid.

2. The method according to claim 1 wherein (I) comprises:
(a) adding Bepromoline hydrochloride to a solution of $FeCl_3$ or $AlCl_3$ in an aprotic solvent at a temperature between 20 and 40° C.;
(b) adding 2-chloro-2-methylbutane, to the mixture obtained from step (a), at said temperature T;
or:
(a') adding concentrated sulphuric acid, to a solution of Bepromoline hydrochloride in an aprotic solvent at a temperature between −10 and 0° C.;
(b') adding 2-methyl-2-butanol, to the mixture obtained from step (a'), at said temperature T;
wherein said steps (b) or (b') are followed by:
(c) keeping said temperature T constant for a time sufficient to alkylate said Amorolfine base.

3. The method according to claim 1 wherein (II) comprises:
(a) dissolving crude Amorolfine base in isopropyl alcohol and adding gaseous hydrochloric acid thereto, and;
(b) crystallizing Amorolfine hydrochloride in said isopropyl alcohol.

4. The method according to claim 2 comprising, after step (c) and before step (II):
(d) adding water to the reaction mixture obtained from step (c);
(e) keeping the temperature below 10° C.;
(f) separating the aprotic solvent phase therefrom;
(g) washing the aprotic solvent phase with a basic aqueous solution;
(h) separating the aprotic solvent phase therefrom;
(i) removing the aprotic solvent by distillation; and,
(j) isolating crude Amorolfine base as an oily substance.

5. The method according to claim 2 wherein the aprotic solvent is methylene chloride.

6. The method according to claim 1 further comprising purifying amorolfine hydrochloride, by:
contacting a solution of crude amorolfine hydrochloride to an HPLC column, said crude amorolfine hydrochloride having purity higher than 90% and containing <5% Bepromoline hydrochloride and <3% Fenpropimorf and a charge ratio of from 70-130 g of stationary phase, per gram of crude amorolfine hydrochloride;
contacting said crude amorolfine hydrochloride with a mobile phase, said mobile phase comprising water and a water miscible organic solvent, said water miscible organic solvent comprising from 5% to 95% by weight of said mobile phase, to elute purified amorolfine hydrochloride therefrom, and
collecting a purified amorolfine hydrochloride which contains less than 0.1 wt. % of each of Bepromoline and Fenpropimorf, and has an HPLC purity grade of more than 99.5%.

7. The method according to claim 6, wherein the stationary phase comprises alkyl ligands having 18 carbon atoms (C18).

8. The method according to claim 6, wherein the amount of organic solvent in the mobile phase comprises 50-90 wt % of said mobile phase.

9. The method according to claim 6, wherein the water miscible organic solvent is chosen from the group consisting of acetonitrile, methanol, propanol, isopropanol, butanol, and t-butanol.

10. The method according to claim 6, wherein when the mobile phase comprises either (i) acidic water buffered with at least one salt, at a pH of 2-7.5, or (ii) water free of any salts.

* * * * *